US00PP16871P3

(12) United States Plant Patent

Iredell et al.

(10) Patent No.: US PP16,871 P3

(45) Date of Patent: Jul. 25, 2006

(54) *BOUGAINVILLEA* PLANT NAMED 'MAUDI'

(50) Latin Name: *Bougainvillea hybrida*
Varietal Denomination: Maudi

(75) Inventors: Peter Iredell, Moggil Brisbane (AU); Jan Iredell, Moggil Brisbane (AU)

(73) Assignee: Bougainvillea Nursery, Queensland (AU)

( * ) Notice: Subject to any disclaimer, the term of this patent is extended or adjusted under 35 U.S.C. 154(b) by 0 days.

(21) Appl. No.: 10/973,065

(22) Filed: Oct. 23, 2004

(65) Prior Publication Data

US 2005/0262610 P1 Nov. 24, 2005

(51) Int. Cl.
*A01H 5/00* (2006.01)

(52) U.S. Cl. ..... Plt./256

(58) Field of Classification Search ..... Plt./256
See application file for complete search history.

(56) References Cited

PUBLICATIONS

UPOV–Rom, Plant Variety Database, GTI Jouve Retreival software, 2005/01, hit on 'Maudi'.*

Plant Varieties Journal, Quarter Two 2002, vol. 15, No. 2, pp. 28–29 and 103.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Bougainvillea* plant named 'Maudi', characterized by its outwardly spreading and bushy plant habit; vigorous growth habit; dark green-colored fully expanded leaves; freely flowering habit; and dark red purple-colored flower bracts.

1 Drawing Sheet

Botanical classification/cultivar designation: *Bougainvillea hybrida* cultivar Maudi.

BACKGROUND OF THE INVENTION

The present Invention relates to a new and distinct cultivar of *Bougainvillea* plant, botanically known as *Bougainvillea hybrida,* and hereinafter referred to by the name 'Maudi'.

The new *Bougainvillea* is a naturally-occurring branch mutation of the *Bougainvillea hybrida* cultivar Zuki, not patented. The new *Bougainvillea* was discovered and selected by the Inventors from within a population of plants of the cultivar Zuki in a controlled environment in Brisbane, Queensland, Australia in 1995. The selection of this plant was based on its attractive flower coloration and non-variegated leaves.

Asexual reproduction of the new cultivar by cuttings at Brisbane, Queensland, Australia since 1996, has shown that the unique features of this new *Bougainvillea* are stable and reproduced true to type in successive generations.

SUMMARY OF THE INVENTION

Plants of the cultivar Maudi have not been observed under all possible environmental conditions. The phenotype may vary somewhat with variations in environment such as temperature and/or light intensity without, however, any variance in genotype.

The following traits have been repeatedly observed and are determined to be the unique characteristics of 'Maudi'. These characteristics in combination distinguish 'Maudi' as a new and distinct cultivar:

1. Outwardly spreading and bushy plant habit.
2. Vigorous growth habit.

3. Dark green-colored fully expanded leaves.
4. Freely flowering habit.
5. Dark red purple-colored flower bracts.

Plants of the new *Bougainvillea* are most similar to plants of the parent, the cultivar Zuki. In side-by-side comparisons conducted in Moggill, Queensland, Australia, plants of the new *Bougainvillea* differed primarily from plants of the cultivar Zuki in leaf coloration as plants of the cultivar Zuki had variegated leaves.

Plants of the new *Bougainvillea* can also be compared to plants of the *Bougainvillea* cultivar Gloucester Royal, not patented. In side-by-side comparisons conducted in Moggill, Queensland, Australia, plants of the new *Bougainvillea* differed from plants of the cultivar Gloucester Royal in the following characteristics:

1. Plants of the new *Bougainvillea* were more compact than plants of the cultivar Gloucester Royal.
2. Plants of the new *Bougainvillea* had glossier leaves than plants of the cultivar Gloucester Royal.
3. Plants of the new *Bougainvillea* flowered more frequently than plants of the cultivar Gloucester Royal.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Bougainvillea.*

The photograph at the top of the sheet is a side perspective view of typical one-year old plants of 'Maudi' grown in containers in an outdoor nursery.

The photograph in the middle of the sheet is a close-up view of typical developing flowers of 'Maudi'.

The photograph at the bottom of the sheet is a close-up view of typical developing leaves of 'Maudi'.

DETAILED BOTANICAL DESCRIPTION

In the following description, color references are made to The Royal Horticultural Society Colour Chart, 2001 Edition, except where general terms of ordinary dictionary significance are used. Plants used for the following botanical description were grown in Moggill, Queensland, Australia in a polyethylene-covered greenhouse. Plants used for the description were about one to two years old.

Botanical classification: *Bougainvillea hybrida* cultivar Maudi.

Parentage: Naturally-occurring branch mutation of the *Bougainvillea hybrida* cultivar Zuki, not patented.

Propagation:

*Type.*—By cuttings.

*Time to initiate roots.*—About one week at 25° C.

*Time to develop roots.*—About two weeks at 25° C.

*Root description.*—Thick; freely branching; white in color.

Plant description:

*Form.*—Outwardly spreading and bushy plant habit; vigorous growth habit. Freely branching with lateral branches potentially developing at every node.

*Plant height, soil level to top of plant plane.*—About 1 to 1.5 meters.

*Plant width.*—About 1 to 1.5 meters.

*Stem color.*—162A.

*Stem texture.*—Smooth, glabrous.

*Thorns.*—Length: About 1.2 cm to 1.8 cm. Diameter: About 1.75 mm to 2 mm. Color: 177B.

*Foliage description.*—Arrangement: Opposite, simple. Length: About 8 cm. Width: About 6.3 mm. Shape: Broadly ovate. Apex: Acuminate. Base: Obtuse. Margin: Entire; slightly undulate. Texture, upper and lower surfaces: Smooth, glabrous. Venation pattern: Pinnate. Color: Developing foliage, upper surface: 147A; towards the center, 147B; "watermark variegation". Developing foliage, lower surface: 144A; towards the center, 145A. Fully expanded foliage, upper surface: 138A; towards the center, 144A; "watermark variegation" not apparent. Fully expanded foliage, lower surface: 147A; towards the center, 147B. Venation, upper surface: 144B. Venation, lower surface: 11D. Petiole length: About 2.4 cm. Petiole diameter: About 1 mm. Petiole texture, upper and lower surfaces: Smooth, glabrous. Petiole color, upper and lower surfaces: 166B.

Flower description:

*Flower type and habit.*—Single flowers arranged in axillary panicles with showy bracts. Flowers face mostly upright. Flowers not persistent.

*Fragrance.*—None.

*Natural flowering season.*—Cyclically flowering year-round in Moggill, Queensland, Australia; flowering periods about 6 to 13 weeks long.

*Quantity.*—Freely flowering with about 35 flowers per panicle.

*Flower longevity.*—About five to eight days.

*Flower diameter.*—About 1 cm.

*Flower depth (height).*—About 1.8 cm.

*Flower buds.*—Length: About 1.4 cm. Diameter: About 2 mm. Shape: Elongated. Color: N144C.

*Petals.*—Quantity per flower: About five; fused tubular corolla. Length: About 3 cm. Width: About 3 mm. Shape: Fan-shaped. Apex: Emarginate. Margin: Entire. Texture, upper and lower surfaces: Smooth; glabrous. Color: When opening, upper and lower surfaces: 158C. Fully opened, upper and lower surfaces: 56A; towards the margins, 50C.

*Sepals.*—Quantity per flower: About five; fused tubular corona. Length: About 1.8 cm. Diameter: About 1 mm. Shape: Linear. Apex: Acute. Margin: Entire. Color: When opening, upper and lower surfaces: 64A. Fully opened, upper and lower surfaces: 64A.

*Flower bracts.*—Quantity per flower: Three. Length: About 3.5 cm. Width: About 3.2 cm. Shape: Broadly ovate. Apex: Acute. Base: Obtuse. Margin: Entire; slightly undulate. Texture, upper and lower surfaces: Smooth; glabrous; rugose. Color: When opening, upper and lower surfaces: 59A to 59B. Fully opened, upper and lower surfaces: 59B; color becoming closer to N66B with development.

*Peduncles.*—Length: About 3 cm. Diameter: About 1.5 mm. Texture: Smooth, glabrous. Angle: About 45° from vertical. Strength: Strong. Color: 166B.

*Pedicels.*—Length: About 1.5 cm. Diameter: About 1 mm. Texture: Smooth, glabrous. Angle: About 45° from vertical. Strength: Strong. Color: 166B.

*Reproductive organs.*—Androecium: Stamens per flower: About eight. Anther shape: Oblong. Anther length: About 0.5 mm. Anther color: 22A. Pollen color: 22A. Gynoecium: Quantity of pistils per flower: One. Pistil length: About 9 mm. Stigma shape: Linear. Stigma color: 6C. Style length: About 3 mm. Style color: 145A. Ovary color: 145A.

*Seeds/fruits.*—Seed and fruit development has not been observed.

Disease/pest resistance: Under commercial production conditions, plants of the new *Bougainvillea* have not been noted to be resistant to pathogens or pests common to *Bougainvillea.*

Garden performance: Plants of the new *Bougainvillea* have good garden performance as plants of the new *Bougainvillea* have been observed to tolerate wind, rain and temperatures from 3 to 40° C.

It is claimed:

1. A new and distinct cultivar of *Bougainvillea* plant named 'Maudi', as illustrated and described.

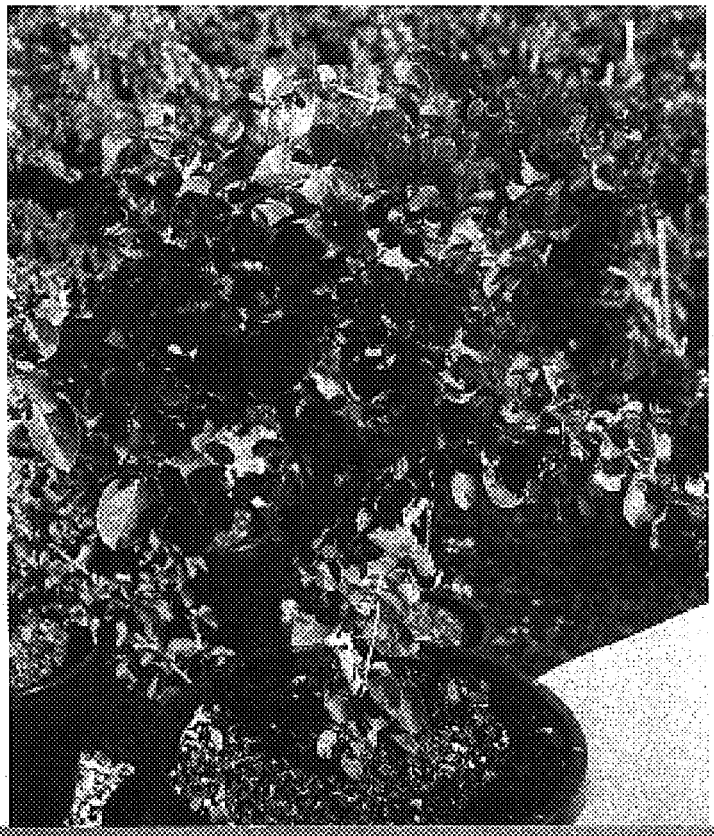
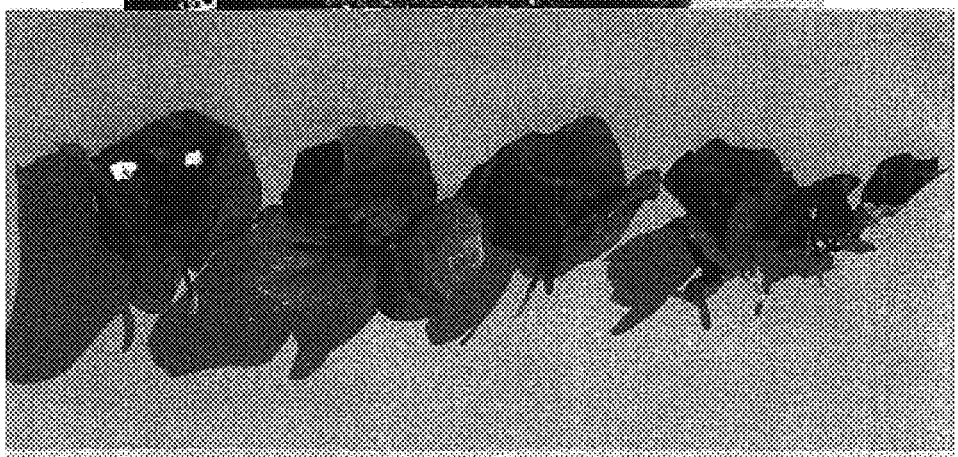
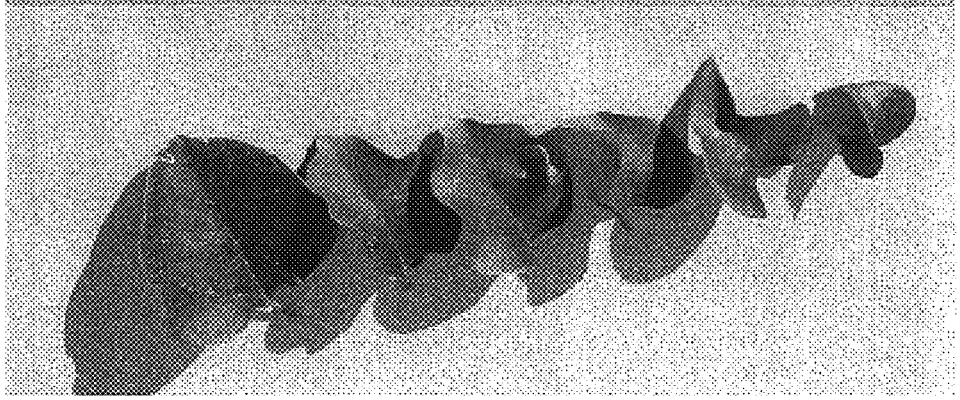

* * * * *